US008822142B2

(12) United States Patent
Deininger

(10) Patent No.: US 8,822,142 B2

(45) Date of Patent: Sep. 2, 2014

(54) ANALYSIS OF SINGLE BIOLOGICAL CELLS

(75) Inventor: Sören-Oliver Deininger, Leipzig (DE)

(73) Assignee: Bruker Daltonik GmbH, Bremen (DE)

( * ) Notice: Subject to any disclaimer, the term of this patent is extended or adjusted under 35 U.S.C. 154(b) by 299 days.

(21) Appl. No.: 12/734,988

(22) PCT Filed: Dec. 9, 2008

(86) PCT No.: PCT/EP2008/010421

§ 371 (c)(1), (2), (4) Date: Jun. 8, 2010

(87) PCT Pub. No.: WO2009/077106

PCT Pub. Date: Jun. 25, 2009

(65) Prior Publication Data

US 2010/0255531 A1 Oct. 7, 2010

(30) Foreign Application Priority Data

Dec. 14, 2007 (DE) ......................... 10 2007 060 438

(51) Int. Cl.
*C12Q 1/00* (2006.01)
*H01J 49/16* (2006.01)

(52) U.S. Cl.
CPC .................................... *H01J 49/164* (2013.01)
USPC ............................................... 435/4; 436/174

(58) Field of Classification Search
USPC ............................................... 435/4; 436/174
See application file for complete search history.

(56) References Cited

U.S. PATENT DOCUMENTS

| | | | | |
|---|---|---|---|---|
| 7,138,625 | B2 * | 11/2006 | Overney et al. | 250/288 |
| 7,145,135 | B1 * | 12/2006 | Overney | 250/288 |
| 7,235,781 | B2 | 6/2007 | Haase | |
| 2005/0056776 | A1 | 3/2005 | Willoughby | |
| 2006/0063145 | A1 | 3/2006 | Suckau | |
| 2008/0142703 | A1 | 6/2008 | Schurenberg | |

FOREIGN PATENT DOCUMENTS

| | | |
|---|---|---|
| GB | 2 422 052 | 7/2006 |
| WO | WO 2006/067495 | 6/2006 |

OTHER PUBLICATIONS

Schwamborn, Kristina et al. Identifying Prostate Carcinoma by MALDI-Imaging. International Journal of Molecular Medicine. 2007. vol. (20). pp. 155-159.*

Sadeghi, Merhrnoosh et al. Crystallite Size Dependence of Volatilization in Matrix-Assisted Laser Desorption Ionization. Elsevier: Applied Surface Science 127-129. 1998. pp. 226-234.*

Fitzgerald, Margaret et al. Cell Structure and Percent Viability by a Slide Centrifuge Technique. Journal of Clinical Pathology. 1982. vol. (35): pp. 191-194.*

Holle, Armin et al. Optimizing UV Laser Focus Profiles for Improved MALDI Performance. Journal of Mass Spectrometry. 2006. vol. (41). pp. 705-716.*

Hillenkamp, Franz. MALDI MS: A Practical Guide to Instrumentation, Methods, and Applications. Wiley-Vch. 2007. pp. 30-32.*

Redeker, Toullec, Vinh. Rossier, Soyez, "Combination of Peptide Profiling by Matrix-Assisted Laser Desorption/ionization Time of Flight Mass Spectrometry and Immunodetection of Single Glands or Cells", Analytical Chemistry, vol. 70, No. 9, May 1, 1998.

R. Garden, L. Moroz, T. Moroz, S. Shippy, J. Sweedler, "Excess Salt Removal with Matrix Rinsing: Direct Peptide Profiling of Neurons from Marine Invertebrates Using Matrix-assisted Laser Desorption/ionization Time-of-flight Mass Spectroemetry", Journal of Mass Spectrometry, vol. 31, 1996, Pa. 1126-1130.

* cited by examiner

*Primary Examiner* — Susan Hanley
*Assistant Examiner* — Nghi Nguyen
(74) *Attorney, Agent, or Firm* — Paul Vincent

(57) ABSTRACT

An analysis of type, state or other distinguishing features of individual cells from body fluids, smears or tissues includes the steps of depositing the cells, with a minimum possible overlap, on a mass spectrometric sample support, determining the coordinates of the cells, coating the sample support with a layer of small crystals of a matrix substance, positioning the cells, inside a mass spectrometer, according to their known coordinates with a movement device into the position of the laser focus, acquiring mass spectra of the individual cells with ionization of the cell components by matrix assisted laser desorption, and using the mass spectra for an analysis of type, state or other distinguishing features of the cells.

16 Claims, 1 Drawing Sheet

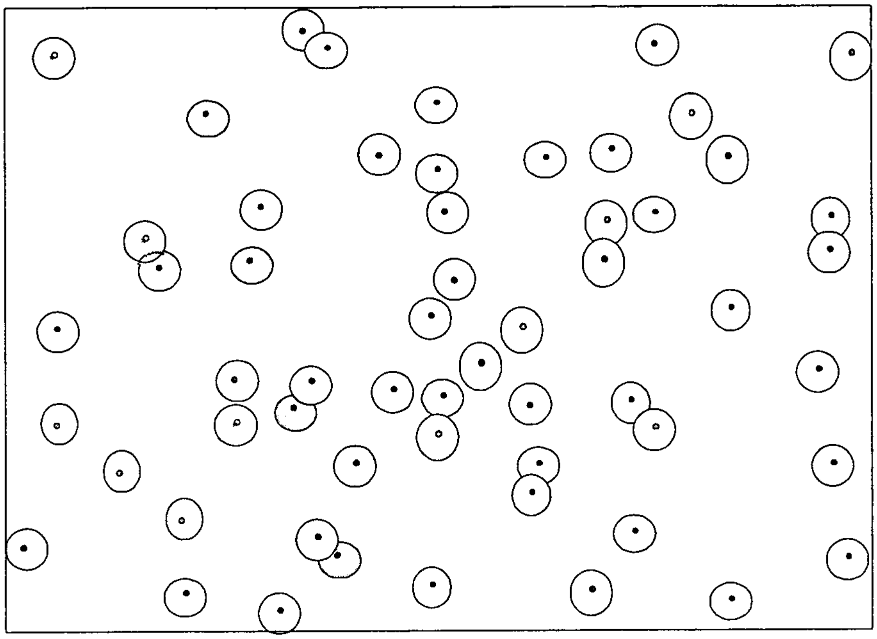

ANALYSIS OF SINGLE BIOLOGICAL CELLS

This application is the national stage of PCT/EP2008/010421 filed on Dec. 09, 2008 and also claims Paris Convention priority to DE 10 2007 060 438.8 filed on Dec. 14, 2007.

BACKGROUND OF THE INVENTION

The invention relates to the analysis of type, state or other distinguishing features of individual cells from body fluids, smears or tissues.

The invention comprises the steps of depositing the cells, with a minimum possible overlap, on a mass spectrometric sample support, determining the coordinates of the cells, coating the sample support with a layer of small crystals of a matrix substance, positioning the cells, inside a mass spectrometer, according to their known coordinates with a movement device into the position of the laser focus, acquiring mass spectra of the individual cells with ionization of the cell components by matrix assisted laser desorption, and using the mass spectra for an analysis of type, state or other distinguishing features of the cells.

Imaging mass spectrometry analysis of thin histologic sections or other flat samples with ionization of the molecules of interest using matrix assisted laser desorption (MALDI) has recently experienced an exceptional increase in popularity. Generally, the method is used to measure distributions of specific proteins which, either alone or in combination with other proteins, can serve as biomarkers for the visualization of various organs and, above all, for characterizing the stress or disease states of individual regions of the flat sample. No other method can at present characterize these stress or disease states as reliably and quickly. A method of this type is described in the patent application DE 10 2004 037 512.7 (D. Suckau et al., GB 2 418 773 A, U.S.-2006-0006315-A1).

In these processes, thin sections are typically applied to special specimen slides, the transparency of which permits microscopic observation and which feature a conductive layer so that later, in the mass spectrometer, they can provide a defined potential for the acceleration of the ions generated there.

The flat sample on the specimen slide must be covered with a layer of small matrix crystals in a special way to ensure that the proteins and also other substances of interest can be ionized effectively. A particularly favorable coating method is described in the patent application DE 10 2006 059 695.1 (M. Schürenberg, GB 2 446 251 A, US 2008/0142703 A1). This fine spraying or misting method is optically controlled, thereby achieving a dense, reproducible coverage with a layer of matrix crystals between 20 and 50 micrometers thick. Protein molecules, in particular, are drawn out of the sample to the surface of the layer. In combination with special laser beam profiles, the matrix layer surprisingly, and contrary to what had previously been believed, demonstrates a very high sensitivity, so that the most important proteins of even very small regions of the thin histologic section can be analyzed. The conventional understanding was that only one analyte ion would be formed from 10,000 analyte molecules. However, for reasons that have not yet been understood, the yield of protein ions from the layer of fine matrix crystals appears to be greater than this by a factor of at least 100, and possibly 1000, when special laser beam profiles are used.

When specially shaped laser beam profiles, such as those presented in the patent application DE 10 2004 044 196 A1 (A. Hase et al., GB 2 421 352 A, US 7,235,781 B2) are used, the analysis of the proteins can be restricted to regions with a diameter of only about five micrometers. The laser beam profile consists primarily of one or more laser beam points, each with a diameter of only five micrometers or less. Due to slight lateral diffusion when the matrix layer is applied, the spatial resolution when measuring the distribution of molecules in the flat samples is usually about 20 micrometers, which is perfectly adequate for the majority of applications.

To obtain a good quality measurement, with high sensitivity and good precision in the measurement of concentration, it is not sufficient, however, to record a single spectrum based on a single laser pulse. Rather, between 20 and 500 individual spectra are added to form a sum spectrum. When the term “mass spectrum” is used below, it is this sum spectrum that is always meant. If the spatial resolution is fully exploited by taking the measurements with a 20 micrometer grid spacing, this means that 250,000 mass spectra, composed of many millions of individual spectra, will be recorded for each square centimeter of thin section. If the recording speed is one mass spectrum per second on the basis of, for instance, 200 individual spectra recorded at 200 Hz, this process will take about 70 hours per square centimeter.

Of course, lower spatial resolutions can also be chosen; for cross-sections taken through the bodies of, for instance, mice or rats, grid spacings of between 200 and 500 micrometers permit a very good distribution of analyte substances across the individual organs and intermediate spaces to be measured. Here only 2500 or 400 mass spectra respectively need to be recorded per square centimeter; these may nevertheless still comprise between a hundred thousand and a million individual spectra. In this case again, the ability to record the individual spectra at a high frequency, preferably more than 1000 individual spectra per second, is desirable. However, these individual spectra must not be taken from a single point to avoid overheating the matrix layer at this site. It is therefore expedient to continuously vary the recording coordinates and, in particularly critical cases, to lower the recording rate down to, for instance, only 200 individual spectra per second.

It is, however, not just the mass spectrometric analysis of the state of tissues from parts of thin histologic sections that is of interest, but also the analysis of individual cells from smears, body fluids or tissues. The analyses may be aimed at determining the type of cells, or may be oriented toward the stress, disease or infection of the individual cells. Even the simple determination of distinguishing features is interesting, and the reasons for the distinguishing features do not even have to be known.

For such an analysis, the cells, if they are not already distributed in body fluids, must be dispersed, separated from one another, in a liquid. Equipment is commercially available specifically for preparing the cells from liquids on specimen slides. Here, the cells are applied to a small region of the specimen slide, for instance one square centimeter, by gentle centrifuging; they are pressed flat without being damaged, and occupy a space with a diameter of about 20 micrometers. Cells from tissues such as bone marrow can also be distributed in liquids, and then applied to specimen slides, using special procedures. If the number of cells in the liquid is small enough, there will be very few overlaps, and the medical professional will be able to observe the cells individually under a microscope. A “small enough number” of cells here means from a few hundred up to a maximum of about 10,000 cells per square centimeter. The optimum for the lowest possible percentage of overlaps is around 3000 cells per square centimeter.

The purpose of such an analysis is often to determine the presence of a few abnormal cells, tumor cells for instance, among a large number of normal cells; this is a laborious and very tiring task if the medical professional has to examine the cells visually. For many of these cases, staining methods are either not known or do often not provide very high contrast; visual detection of tumor cells is affected by a large number of subjective influences and it is hard to achieve an objective analysis. Therefore, automatable methods for this task are required.

Areas of tissue with abnormal cells, tumor cells for instance, in thin sections can, in principle, be recognized as such on the basis of their mass spectra, although these tissue regions are usually mixed with a large proportion, often up to 80%, of healthy cells. An obvious solution is to coat the specimen slide, to which the cells have been applied, with matrix material, in the same way as thin sections, and then to scan them in a mass spectrometer on a grid pattern in order to obtain mass spectra of the individual cells. If all the individual cells, without exception, are to be analyzed, the grid spacing must be dense, having a pitch of at most 20 micrometers. On an area of one square centimeter, this leads to the number, as mentioned above, of 250,000 mass spectra, incorporating millions of individual spectra, and to the time, also mentioned above, of 70 hours, even though there may only be about 1000 to 10,000 cells on the surface. The vast majority of the mass spectra are empty.

Methods of this sort are only possible if solid-state lasers are used. The nitrogen lasers mostly used until now have a life time of only about one million laser pulses. Solid-state lasers have a considerably longer life time, but require special beam shaping measures, which can, however, be designed in a way that is advantageous to the analysis. Mass spectrometers that operate with solid-state lasers are already commercially available.

When referring here to the "state of the cells", this should be understood in the sense of a stress, a pathologic change, an infection or other change from a normal metabolic state of the same type of cell. As has already been explained, tumor cells are of particular significance to this method; tumorous tissue can be clearly distinguished from healthy tissue by mass spectrometry. In general terms, it must be possible to recognize the state from the pattern of substance concentrations that can be detected in the cell by mass spectrometry. The substances may be peptides or proteins that are under- or overexpressed, so creating a characteristic pattern. They may, however, also be post-translational modifications of proteins or decomposition products (metabolites), or accumulations of other substances, such as lipids in the tissue.

The objective of the invention is to analyze type and state of individual cells with a maximum possible degree of automation.

SUMMARY OF THE INVENTION

The invention exploits the surprising recognition that individual cells can in fact be analyzed by mass spectrometry. Using the measures described above, the sensitivity of the mass spectrometric detection can be increased to a point where evaluable mass spectra can be obtained from the mere $10^8$ protein molecules in a cell, with about $10^7$ molecules for the most common protein and only about $10^5$ molecules for a protein at a desired limit of detection.

The invention comprises the steps of depositing the cells, with the minimum possible overlap, on a support plate, determining the position coordinates of the cells, covering the support plate with a layer of small matrix crystals, moving the cells inside the mass spectrometer to the position of the laser focus, acquiring individual mass spectra of the individual cells by ionization of their ingredients through matrix assisted laser desorption, and using the mass spectra to analyze the cells. The analysis can be oriented toward types, states or other distinguishing features of the individual cells. The state can be a result of stress, disease or infection.

The mass spectra of individual cells in different states differ more distinctly from one another than the mass spectra from tissue regions in thin sections, since the latter generally contain mixed spectra. The mass spectra from isolated tumorous and healthy individual cells thus differ even more sharply than equivalent tissue regions in thin sections.

Through favorable shaping of the beam, the recording time for 3000 sum spectra of 3000 cells, at a recording rate of only 200 single spectra per second, can be held to 20 minutes; at higher laser pulse rates, the times are even shorter.

The cells can be applied to the support plate by gentle centrifuging, for which purpose devices are commercially available. Specially prepared specimen slides can, for instance, be used as the support plate. The cells can, however, be applied using other techniques, such as simply by wiping or sedimenting. In order to determine the position coordinates, microscopic recordings or digital contact pictures according to the prior art are particularly suitable; here again, simple technical devices are on the market. The contrast can be heightened by staining, or in the case of microscopic recordings, by dark field illumination or phase contrast. Staining techniques and agents that do not interfere with MALDI are known. Image analysis programs for this purpose can determine not only the position coordinates of the cell centers, but also other parameters such as diameter or overlap parameters. Image evaluation programs even may differentiate between relatively few interesting cells and a vast majority of other cells, either by seize, color, or shape, in order to accelerate the diagnosis process. Commercial devices are available for applying the matrix layer; however, depending on the methods used, the devices give different sensitivities as a result of differing ionization yields. MALDI mass spectrometers are also commercially available that offer sufficient precision for movement of the specimen slide and also a high enough speed for recording the mass spectra.

Suitable programs are also available for determining the state of the cells and other distinguishing features on the basis of the spectral data. The state can finally be read from a state value or state vector on a one-dimensional or multi-dimensional state scale; the calculation of the state value or vector is based on the presence or absence of the signals for individual proteins, and from the intensity ratios between the signals. The calculation of a state value may employ quite complicated expressions involving the signal intensities $I(m)$, where $I$ represents the intensity and $m$ the mass of the ions associated with that signal.

The method by which the state value is calculated may be specified as a parameterized formula, but may on the other hand use a class-generating mathematical-statistical analysis, with or without initial instruction (supervised or unsupervised learning programs). State values or state vectors can be used for depicting the states in false color on a microscopic image.

BRIEF DESCRIPTION OF THE DRAWING

FIG. 1 shows a detail of a support plate with cells that have been applied by gentle centrifuging. Each of the flattened, almost circular, cells has a nucleus located near the center of the cell. In this figure, the cells have a very uniform shape, in other cases, the cells may have quite different shapes, colors, or sizes.

DESCRIPTION OF THE PREFERRED EMBODIMENT

The invention may be primarily directed to the determination of the type or the identity of the cells, meaning the organ or tissue type from which they come. The mass spectra of the cells usually reveal their origin, which can often be narrowed down very precisely to a particular subregion or organelle of an organ.

Furthermore, the invention may serve to determine the state of an individual cell, caused by a particular growth age, nutrient, chemical or physical stress, degeneration by a disease, or infection. Chemical stress can, for instance, be generated by drugs, and physical stress by the effect of temperature or radiation; both can lead to major cell damage.

The invention may be used to investigate a large number of individual cells for known or unknown, even previously undiscovered, differences between different classes of cell. The differences between the classes can be automatically identified by statistical programs on the basis of various features that appear in the mass spectra. The differences in these features may be attributed to various subspecies of the cells of a tissue or organ, to differences in their function, or to other differences in the cell state, such as those resulting from different diet or stress.

The types of cells and many of their states and other features are reflected in the quantitative—or even qualitative—composition of the substances in the interior of the cells, so that in almost all cases these differences can be detected in MALDI mass spectra.

The invention is, for example, of particular importance for the automated detection of tumor cells, particularly the detection of a very small number of tumor cells among a vast majority of healthy cells. It is surprising that from the constituents of a single cell, in particular the proteins, ionization by matrix assisted laser desorption can yield mass spectra offering such effective analysis procedures that a task of this nature can be accomplished.

The invention essentially consists in analyzing individually a large number of biological cells, comprising the following steps:

a) applying the cells to a support plate;
b) determining the position coordinates of the cells;
c) applying a layer of crystals of matrix material;
d) acquiring individual mass spectra of at least a proportion of the individual cells utilizing the position coordinates, with ionization of the cell constituents by matrix assisted laser desorption; and
e) evaluating the mass spectra to determine type, state or other characteristic features of the cells.

In step a) the cells are applied, as isolated as possible from one another, to a support plate such as a specimen slide that can also be used as a mass spectrometric sample support. In order to provide a defined electrical potential in the mass spectrometer, the surface of the support plate should be electrically conductive. But the support plate does not have to be transparent; other support plates, such as metal plates, can be used, provided it is possible to attain sufficiently good images of the applied cells.

The cells can be applied in step a) using a method such as moderate centrifuging from a liquid; directly from body fluid for instance. At this stage it is necessary to ensure that no more than about 10,000 cells are applied to each square centimeter in order to keep the number of overlaps small. A figure of around 3000 cells per square centimeter is favorable, but there are also other useful diagnostic or research applications in which only about a hundred or fewer cells are applied. The cells may already be contained in the fluid when it is removed from the body, or may be added to the fluid as separated tissue cells, as in the case of the cells from bone marrow biopsies. Tissue cells may be separated by dissolving the intercellular bonds, e.g., by enzymatic separation. The cells may, furthermore, be selected using a cell sorter, although this is not necessary. The mild centrifugation presses the cells flat onto the support without damaging them; they thus adopt an almost circular form with a diameter of about 10 to 25 micrometers, with the cell nucleus almost exactly in the center of the cell. The applied cells are usually then dried, as a result of which they are bonded firmly to the support plate.

In step a) the cells may also be applied using other methods such as wiping, simple sedimentation of a fluid with subsequent decanting and drying, or by laser-assisted microdissection. Here too, the drying causes the initially loose cells to shrink, flatten and adhere to the support.

Once cells have been applied to the support plate, they can be observed with optical means, such as a microscope. A schematic picture of very uniform cells on a sample support is shown in FIG. 1; the cells, however, might not be that uniform in other cases. Stains can be applied to raise the contrast; staining agents are known which do not interfere with mass spectrometric recordings taken with MALDI. A microscope with dark field illumination, which shows the cells bright against a dark background, is particularly favorable. Digital images can be produced by microscopic photography, or by direct contact taken in relatively simple devices; a resolution of about two micrometers should preferably be achieved. Such digital images can be employed to determine the position coordinates of the cells.

Image-evaluating computer programs are known and widely used. They can be used to determine the center of the circular cells as well as other parameters such as the diameter, non-circularity, and the degree and direction of overlap. The position coordinates and any other associated parameters are stored in a computerized list, which is later used as the basis for measuring the mass spectra. The position coordinates are referenced to special marking points on the support plate, which can also be detected during the subsequent mass spectrometric measurement.

Image evaluation also may be used to search for, select, and mark particularly interesting subgroups of cells among large numbers of "normal" cells, if these are visually recognizable. Marking the interesting cells may shorten considerably the mass spectrometric analysis. The selection may refer to size, shape, or color of the cells, possibly after staining. An example may be the selection of the subgroup of a particular type of stainable leukocytes in blood which consists mainly of an overwhelming majority of erythrocytes.

Once the list of position coordinates has been created, the support plate—with the cells applied to it—can be coated in an appropriate way in step c) with a layer of small matrix crystals. A favorable method is described in the patent application DE 10 2006 059 695.1 (M. Schürenberg), cited above. Here, clouds of separate mist droplets of matrix solution are deposited onto the support plate, from which extremely fine matrix crystals form during the drying process, and each layer is almost completely dried. The process is controlled by measuring scattered light. The repeated application of layers of separate mist droplets causes proteins to be extracted from the cells and, so it appears, to be transported in a very purified form to the surface of the crystal layer, as a result of which ionization in the MALDI process produces an extremely high yield of protein ions. At the end, the support plate looks like a landscape covered with fine frost; the cells are no longer visible. The thickness of the layer depends on the optimum ionization yield and, astonishingly, is relatively thick, at about 20 to 50 micrometers. The lateral diffusion of the proteins is relatively low, being less than 15 micrometers.

Mass spectrometric measurement of the protein profiles is favorably carried out in the mass spectrometer's vacuum, although reasonably successful tests have generated ions outside the mass spectrometer in the ambient gas using MALDI. In-vacuum MALDI time-of-flight mass spectrometers are usually equipped with sufficiently precise movement devices for the support plates.

The individual cells, whose position coordinates are known, are moved by the movement device of the mass spectrometer's ion source to the focus location of the firmly mounted pulsed UV laser. A choice can be made between only measuring the completely isolated cells or also measuring the cells that overlap by not more than a given threshold. In the case of overlapping cells, the lateral diffusion of the protein molecules can easily result in mixed spectra, which may not deliver any conclusive findings. When cells overlap, it is possible to approach the cells decentrally in such a way that mixed spectra are avoided as far as possible. With very large cells it has been proved favorable to avoid moving to the center of the cell, as this is where the nucleus is located in the great majority of cases; the signals from the nucleus can mask the proteins of the cell.

Pulsed UV lasers with pulse durations of between 0.1 and 10 nanoseconds are used for the ionization. Short laser pulses below one nanosecond are preferred because they increase the ion yield. Special lenses allow laser focus diameters of 5 micrometers or less; it is also possible to generate either one or several simultaneously occurring focal points. For the present task it is, for instance, favorable to use three or four focal points arranged as a triangle or square, with their center points about 10 micrometers apart, since the absolute number of ions formed rises with the number of focal points. More focal points than this should not, on the other hand, be used, as it is then no longer possible to aim at a single cell. The laser focal points should each be moved a little from one pulse to the next, so that the conglomerate of matrix crystals does not melt. The matrix crystals have diameters of roughly one micrometer. A type of movement that preferably sweeps the area of the cell uniformly in consecutive laser pulses should be generated, for example a circulating cycloidal movement.

The use of four focal points allows the number of individual spectra needed to generate a nicely evaluable mass spectrum to be reduced to around 50 laser shots. At a laser pulse rate of 200 Hz, it is therefore possible to record about three mass spectra, belonging to three cells, each second, including the transit times of the sample support plate. If 3000 cells are applied to a support plate, about 20 minutes are therefore required to record the mass spectra of all the cells. These are very acceptable times that make the routine application of the method worth recommending. Times like this can compete with visual inspection, in addition to which the method is less tiring. Above all, the method is more objective and is entirely reproducible. The probability of a false determination is significantly reduced. There is no longer any question of willful decisions.

Programs for evaluating the mass spectra have been developed which up to now have been used for imaging mass spectrometry on thin tissue sections. These programs thus correspond to the prior art, and are familiar to those skilled in the art. They can, for instance, characterize certain states of the cells of a tissue using the value scale of the state values or, in the case of multi-dimensional evaluation, the value scale of the state vectors; the state values are calculated as mathematical expressions, which can be composed in any desired way from the signals I(m). The state values can be one-dimensional or, as state vectors, may also be multidimensional, which allows assignment to various type and state classes. The most favorable form of the mathematical expressions for calculating the state values can be obtained from a mathematical-statistical analysis of mass spectra obtained from precisely characterized cells of different types or states.

The programs for evaluating the mass spectra can also use mathematical/statistical routines that are able independently to determine classes on the basis of various characterizing features, to calculate class-generating expressions for the distinguishing features. It is possible here to specify classes, for example by marking the cells concerned on the digitally displayed image ("supervised learning programs"). Other programs form classes autonomously ("unsupervised learning programs", "cluster analysis"). These methods also belong to the prior art.

The term "mass spectrum" is often used here to refer to a protein profile. It should, however, be noted that the profiles may relate to substances that are not proteins, or that include other substances in addition to proteins. Lipids, for instance, are often found, and these are also known to yield a characteristic pattern for tumorous material. The terms "protein profile" and "proteins of the cell" should therefore always be understood as potentially including other substances.

Determination of the state of individual cells is not, however, restricted to the discovery of tumorous cells. Infected cells, such as those infected by viruses, Chlamydiae or Rickettsia, may also be found. Cells that have died can also be detected and in many cases it is even possible to determine the reason for the death of the cell.

The method according to the invention allows the type, origin or state of an individual cell to be investigated; the most important states of interest are pathologic or infectious abnormalities, most particularly tumor-like abnormalities. The advantage lies in the objective assessment, not involving the usual room for subjective opinion. Tumorous cells can, in almost all cases, be very clearly detected on the basis of their mass spectra, even more clearly than has until now been the case for tissue regions in thin sections, since these regions always contain healthy cells as well, and therefore deliver mixed spectra.

The method opens up another prospect: the specimen slides to which cells have been applied can be carefully washed with solvent in order to remove the layer of matrix crystals. Then, in spite of the recording of the mass spectra that has taken place in the meantime, a condition very close to the original is restored. Damage to the cells, and the extraction of part of their constituents, is practically undetectable. This specimen can now be stained by any appropriate dying method, and is then available for visual checks, or for teaching or study purposes. The visual checks can now be done in the knowledge of the mass spectrometric investigations. It is, in particular, possible to study the visual appearance of different cell states.

A recording of this image can, like the original image of the cells that was used to determine the position coordinates, be overlaid with an image in false color, reflecting the types or states of the cells, as is usual for thin sections. In particular, the cells—either in the image that has been obtained after the mass spectrometry or in the original image—can be colored with false colors according to their type or state, thus making the types or states of the cells visible. These images can, in particular, be displayed very impressively on computer screens, for instance on the screen of the computer that also calculates the assignment of the types or states.

The method has the potential to develop into a standard procedure for the examination of individual cells.

The method indicated here can be modified in many ways by a person skilled in the art who has knowledge of the invention. Some of these modifications have already been indicated above; there are, however, certainly other variations that can generate the desired, information-rich mass spectra for individual cells required to identify their type or their state on the fundamental basis of their separate deposition followed by determination of the position coordinates. These modified methods are included in the invention.

I claim:

1. A method for the analysis of biological cells, the method comprising the steps of:

a) providing multiple separated cells from a body fluid, a smear or a bone marrow;

b) depositing individual cells provided in step a), with minimum possible overlap, to a support plate by gentle centrifuging, wiping or sedimenting;

c) recording an image of the individual cells deposited in step b);

d) determining position coordinates of the individual cells relative to the support plate using the image recorded in step c);

e) covering, following step c), the support plate with a layer of crystals of matrix material, wherein the individual cells are not visible through the matrix material;

f) acquiring, following step e), individual mass spectra of the individual cells utilizing the position coordinates determined in step d), with ionization of the cell constituents by matrix assisted laser desorption; and g) evaluating the mass spectra acquired in step f) to determine types, states or other characteristic features of the individual cells.

2. The method of claim 1, wherein the support plates are specimen slides.

3. The method of claim 1, wherein the cells on the support plate are stained.

4. The method of claim 1, wherein the image is obtained with a microscope.

5. The method of claim 4, wherein the image is obtained by using dark field illumination or phase contrast.

6. The method of claim 1, wherein subgroups of the deposited cells are selected according to their size, shape, or color, and marked for mass spectrometric analysis.

7. The method of claim 1, wherein small matrix crystals are applied by depositing and drying a mist of matrix solution.

8. The method of claim 1, wherein the ionization of the constituents of a cell is achieved by matrix assisted laser desorption using a pulsed UV solid-state laser with a shaped beam profile.

9. The method of claim 8, wherein the beam profile contains a number of adjacent fine focal points.

10. The method of claim 1, wherein the mass spectrum of an individual cell consists of the sum of between 20 and 500 singly acquired mass spectra of the cell.

11. The method of claim 10, wherein a state value or a state vector that characterizes the type, state or other distinguishing features of the cell is calculated from the mass spectrum of each cell.

12. The method of claim 1, wherein following a mass spectrometric analysis of the individual cells, the layer of matrix crystals is removed from the support plate, so that the individual cells are available for visual examination in the knowledge of the results of the mass spectrometry.

13. The method of claim 12, wherein the individual cells are available for visual examination in the knowledge of the results of the mass spectrometry following staining thereof.

14. The method of claim 1, wherein the individual cells on an image of the individual cells on the support plate are given false coloration according to their type or state, thus making the types or states of the cells visible.

15. The method of claim 1, wherein the analysis of the mass spectra in step g) also includes determination of known or formerly unknown consistent cell classes.

16. The method of claim 1, wherein the position coordinates are related to reference positions that can also be detected in a mass spectrometer.

* * * * *